United States Patent [19]

Brown et al.

[11] Patent Number: 5,325,975
[45] Date of Patent: Jul. 5, 1994

[54] SUTURE DISPLAY CABINET

[75] Inventors: David L. Brown, Wallingford, Conn.; Guenter Mattke, Hilton, N.Y.; Peter J. de Leon, Westport, Conn.

[73] Assignee: United States Surgical Corporation, Norwalk, Conn.

[21] Appl. No.: 715,470

[22] Filed: Jun. 14, 1991

[51] Int. Cl.5 ................................................ A47F 5/00
[52] U.S. Cl. ..................................... 211/189; 211/194
[58] Field of Search ................ 211/189, 194; 312/107, 312/108, 111

[56] References Cited

U.S. PATENT DOCUMENTS

| | | |
|---|---|---|
| D. 259,604 | 6/1981 | Schuler et al. . |
| D. 260,955 | 9/1981 | Schuler et al. . |
| 302,624 | 7/1884 | Dickinson . |
| 487,460 | 12/1892 | Wernicke . |
| 902,347 | 10/1908 | Tillinghast . |
| 1,343,423 | 6/1920 | Todd . |
| 1,375,901 | 4/1921 | Drew . |
| 1,399,906 | 12/1921 | Todd . |
| 1,898,056 | 2/1933 | Johnson . |
| 1,936,458 | 11/1933 | Matsen . |
| 2,350,487 | 6/1944 | Bales . |
| 2,455,685 | 12/1948 | Lehman . |
| 2,801,753 | 8/1957 | Shaw . |
| 2,882,114 | 4/1959 | Sease et al. . |
| 3,224,822 | 12/1965 | Kirby . |
| 3,514,170 | 5/1970 | Shewchuk . |
| 3,743,372 | 7/1973 | Ruggerone . |
| 3,836,008 | 9/1974 | Mraz . |
| 3,851,938 | 12/1974 | McCowan et al. . |
| 3,999,818 | 12/1976 | Schankler . |
| 4,005,841 | 2/1977 | Rensland et al. ............ 248/188.9 X |
| 4,123,125 | 10/1978 | Andry, III . |
| 4,155,452 | 5/1979 | Wettermann et al. . |
| 4,199,070 | 4/1980 | Magnussen, Jr. ................ 211/189 X |
| 4,331,335 | 5/1982 | Starkweather . |
| 4,365,709 | 12/1982 | Lester . |
| 4,405,044 | 9/1983 | Flower et al. . |
| 4,485,930 | 12/1984 | Savelkouls . |
| 4,538,726 | 9/1985 | Pastva . |
| 4,586,614 | 5/1986 | Ger . |
| 4,592,601 | 6/1986 | Hlinsky et al. . |
| 4,630,740 | 12/1986 | Belokin, Jr. . |
| 4,767,022 | 8/1988 | Oldorf . |
| 4,775,057 | 10/1988 | Zingeser . |
| 4,796,763 | 1/1989 | Franklin et al. . |
| 4,809,847 | 3/1989 | Schneider . |
| 4,813,553 | 3/1989 | Franklin et al. . |

FOREIGN PATENT DOCUMENTS

| | | |
|---|---|---|
| 0356543 | 10/1990 | European Pat. Off. . |
| 3802228.5 | 2/1988 | Fed. Rep. of Germany . |
| 2443821 | 12/1978 | France . |
| 2488880 | 2/1979 | France . |
| 2092440 | 8/1982 | United Kingdom . |

Primary Examiner—Robert W. Gibson, Jr.
Assistant Examiner—Sarah A. Lechok

[57] ABSTRACT

A suture display cabinet having a plurality of interconnected suture display boxes and suture storage boxes. The boxes are connected to each other through integral dovetail connection members which secure suture display boxes to suture storage boxes and suture display boxes to each other in a side by side arrangement. Various modifications are presented to facilitate transportation of the suture display cabinet from place to place in a surgical environment.

16 Claims, 6 Drawing Sheets

SUTURE DISPLAY CABINET

BACKGROUND OF THE INVENTION

1. Field of the Invention

The present invention relates to display cabinets, and more particularly to display cabinets for surgical instruments or packages such as suture packages, where the cabinets are modular in construction and which may be provided with means for transporting the cabinets to and from and within surgical environments.

2. Discussion of the Prior Art

Display cabinets and racks for storing and displaying surgical instruments such as sutures and suture packages are well known in the art. These cabinets and racks generally comprise conventional shelving which may be separated into individual compartments and constructed as a large semi-permanent structure. Typically, the structures include a back wall which is generally positioned against a wall in either a free-standing position, or which maybe hung on the wall with mounting brackets or screws. A top wall, a bottom wall, and two side walls usually complete the structure, and numerous horizontal and vertical partitions are provided to separate the cabinet into individual compartments. The structures are very cumbersome, and are usually provided as permanent fixtures in a surgical environment.

Also known in the art are modular-type suture display and storage boxes which generally comprise a plurality of small stackable boxes which may be arranged in rows or columns either as a free-standing structure or where the individual boxes are mounted in an array on a wall as individual components. The modular structures also become semi-permanent, in that they are generally not connected to each other and, therefore, cannot be moved without risk of toppling all or part of the structure. Since the structures are impractical to move, they require positioning near the surgical location to allow access to the surgical personnel during an operation. However, this creates a crowded working environment and reduces the freedom of movement which the surgical team requires to perform most operations. Locating the suture display structures remote from the operating table necessitates a surgical team member to be designated as the messenger for retrieving the sutures, thus reducing the efficiency of the surgical team.

U.S. Pat. No. Des. 259,604 and U.S. Pat. No. Des. 260,955, both to Schuler et al. disclose modular suture cabinet boxes which appear to be of the stackable type which are not interconnected to form a transportable unit. There appears to be no means for connecting individual suture boxes to adjacent boxes, other than mounting each box in an array on the wall through a plurality of holes formed in the back of the box.

U.S. Pat. No. 4,592,601 to Hlinsky et al. discloses a modular storage system in which two connected storage boxes are connected to each other by a hook and groove arrangement at the corner of each box. However, each box shares at least one wall with its adjacent boxes, so that individual boxes cannot stand alone. Furthermore, a drawer system is provided to create a closed storage system. Furthermore, the system does not appear to be portable, in that there are no means to move the connected boxes from place to place.

Modular storage and display racks are disclosed in U.S. Pat. No. 4,796,763 and U.S. Pat. No. 4,813,553 to Franklin et al. These patents disclose display racks having a box-like outer container which is provided with a plurality of horizontal shelves and vertical partitions. These outer boxes are then stacked together in an upright free-standing display rack, with the boxes being connected only by the rack itself and not to each other. The racks do not appear to be portable, and are apparently constructed for displaying items in supermarkets or department stores.

SUMMARY OF THE INVENTION

The present invention provides a modular suture display cabinet which utilizes individual suture display boxes and suture storage boxes for creating an interconnected and thus portable suture-display cabinet. Each individual box is dimensioned to hold at least one column of individual suture packages which are stacked one on top another, and additional shelves may be added or removed to provide for varied display and storage capabilities.

The device of the present invention also provides a number of novel means for transporting and moving the suture display cabinet from place to place in a surgical environment such as an operating room.

The device of the present invention comprises at least one surgical suture display box having two side walls, a back wall, a top wall and a bottom wall. The device may include a surgical suture storage box which is provided with a top and bottom wall having similar dimensions to the top and bottom wall of the suture display box, as well as a pair of side walls and a back wall. The suture storage box accommodates individual sutures and other surgical equipment, while the surgical suture display box is constructed to accommodate at least one column of individual surgical suture packages stacked one on top of another. The interior walls of the side walls are provided with grooves to accommodate a horizontally positioned shelf which may be flat or include a series of vertical partitions.

The side walls and top and bottom walls of the surgical suture display box, as well as the top and bottom walls of the surgical suture storage box are each provided with a dovetail connection device which projects outwardly from the top wall and inwardly from the bottom wall. One of the side walls is provided with an outwardly projecting dovetail member, while the opposite side wall is provided with an inwardly directed dovetail device so that a plurality of suture display boxes may be connected side to side. The surgical suture storage box is provided with a top wall having an outwardly directed dovetail connection member, while the bottom wall of the suture storage box is provided with an inwardly directed dovetail connection member. The storage box connects to the bottom of the display box, and provides for vertical stacking of surgical suture storage and display boxes.

In the preferred embodiment, a plurality of suture storage and suture display boxes are interconnected. Although the boxes may be connected in any combination of individual boxes, it is preferred that the boxes are connected in at least two rows. The rows may be stacked vertically, in that at least two rows of three boxes each are provided in an array of six individual boxes to form the cabinet. In one embodiment, a handle member may be connected to the cabinet, preferably at the back wall of the upper row of suture display boxes, to allow the cabinet to be transported about a surgical room. Preferably, the back walls of each of the suture display boxes are provided with several key hole type slots for mounting the handle thereto.

In a second embodiment, two rows of boxes may be positioned back to back so that preferably a row of three suture display and storage boxes are positioned back to back with a second row of suture display and storage boxes to form a back to back array of six boxes. A handle may be provided which is positioned between and secured to the two rows along the respective back walls, to facilitate transporting the cabinet from place to place in an operating room. Preferably, two rows of six storage and display boxes are positioned back to back with a second set of two rows of suture storage and display boxes to form a block of twelve. A handle member is preferably positioned between the two blocks of six and secured to the abutting back walls.

In another embodiment, at least one row of three suture display and storage boxes are positioned back to back with a second row of three suture display and storage boxes and positioned on a tray device having handles for carrying the cabinet from place to place. Alternately, the tray may be provided with a revolving turntable-type pedestal to allow the cabinet to be rotated in place to access all parts of the cabinet. Additionally, it is contemplated that the tray be provided with means for accepting an extended pole member which attaches to the bottom of the tray and terminates in a pedestal base having casters for wheeling the cabinet about an operating room. The pole may be telescopic to allow for adjustment of the height of the pole thereby adjusting the height of the cabinet to best suit the surgical team. Also, the pole may be eliminated and the casters be provided directly on the tray.

BRIEF DESCRIPTION OF THE DRAWINGS

The foregoing features of the present invention will become more readily apparent and may be understood by referring to the following detailed description of an illustrative embodiment of the surgical suture display cabinet, taken in conjunction with the accompanying drawings, in which.

DETAILED DESCRIPTION OF THE PREFERRED EMBODIMENTS

Figure 1:
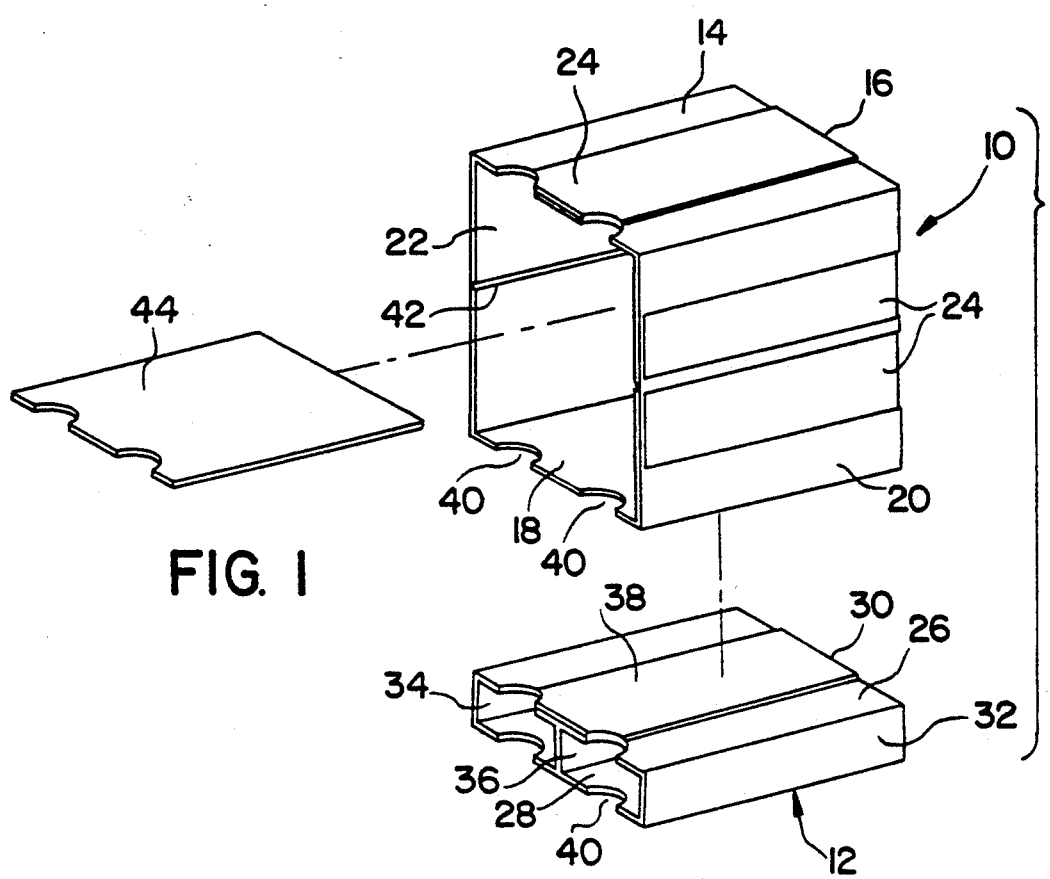
FIG. 1 illustrates an exploded perspective view of a suture display box and a suture storage box which form the essential components of the suture display cabinet of the present invention.

Referring now in specific detail to the drawings, in which like reference numerals identify similar or identical elements throughout the several views, FIG. 1 illustrates the basic essential components which make up the suture display cabinet of the present invention. Suture display box 10 is shown, which is preferably constructed of rigid plastic material but may be constructed of any rigid construction material. Suture display box 10 includes top wall 14, back wall 16, bottom wall 18, and side walls 20 and 22. A suture storage box 12 is also shown in FIG. 1, which is constructed of a similar material as suture display box 10. Suture storage box 12 is constructed of top wall 26, back wall 30, bottom wall 28, and side walls 32 and 34. A vertical upstanding partition 36 separates the interior cavity of suture storage box 12 into two components as shown. A removable shelf 44 may be slid into grooves 42 on the interior of walls 20 and 22 of suture display box 10 to further partition the interior cavity of suture display box 10.

Preferably, suture display box 10 is dimensioned so as to accommodate at least one vertically disposed column of individual suture packages, and preferably may accommodate two side by side columns of suture packages. Suture storage box 12 is dimensioned so as to hold individual packages of sutures which may have been removed from the stacks positioned within suture display box 10. Semi-circular cutout portions 40 are positioned in the top and bottom walls of both suture display box 10 and suture storage box 12, as well as the front face of shelf 44 to provide easy gripping access to the sutures stored therein. Preferably, cutouts 40 are aligned from top to bottom along the same axes.

Top wall 14, bottom wall 18, and side walls 20 and 22 of suture display box 10 are provided with at least one dovetail connection member 24 to secure suture display box 10 to adjacent boxes to construct the suture display cabinet of the present invention. Suture storage box 12 is provided with dovetail connection members 38 on top wall 26 and bottom wall 28 to facilitate attaching suture storage box 12 to the top or bottom wall of adjacent suture display boxes 10.

Figure 2:
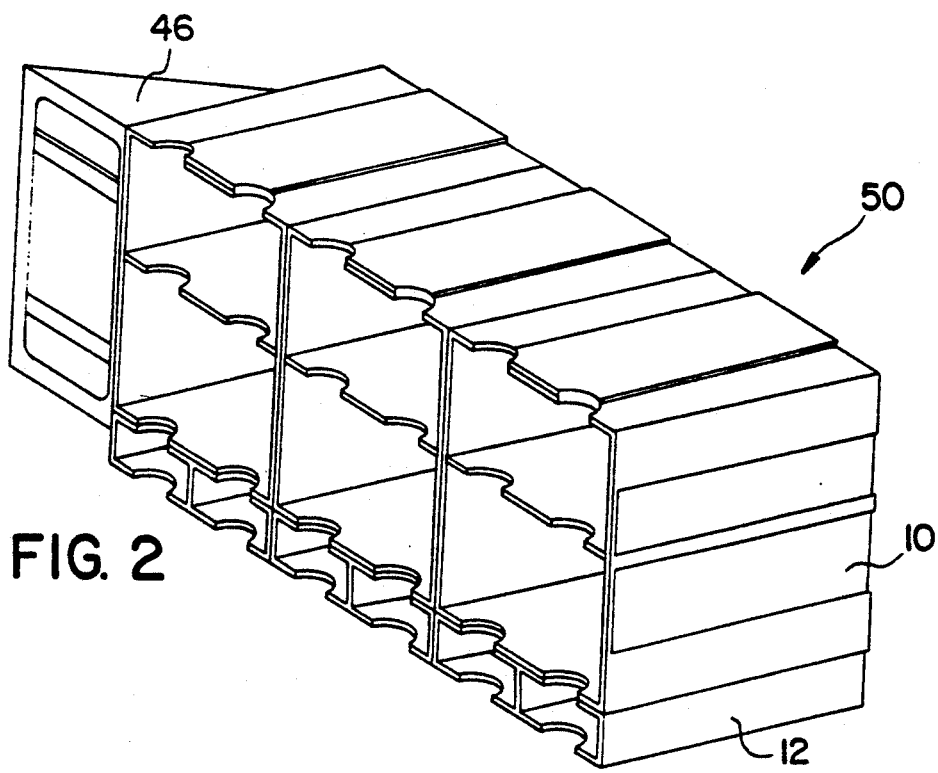
FIG. 2 illustrates a perspective view of a typical suture display cabinet according to the present invention.

FIG. 2 illustrates suture display cabinet 50 according to the present invention. A plurality of suture storage boxes 12 are secured to the bottom wall of a plurality of suture display boxes 10, and adjacent suture display boxes 10 are secured to each other through the provision of dovetail connection members 24. A corner bracket member 46 may be provided to align additional suture display cabinets at right angles to each other.

Figure 3:
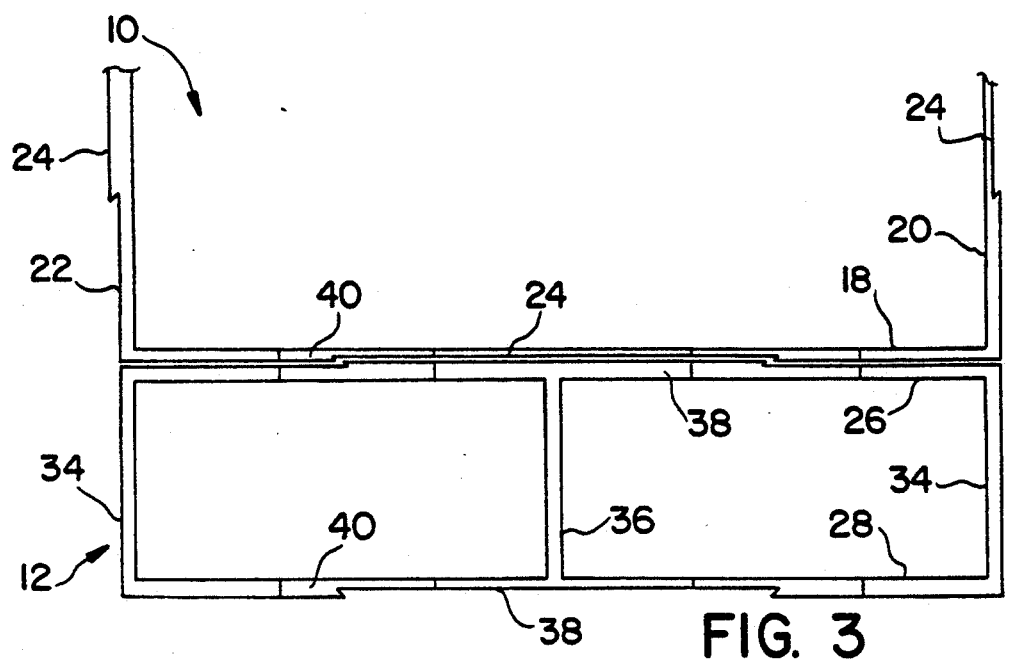
FIG. 3 illustrates a front plan view of a suture storage box connected to the suture display box forming part of the suture display cabinet of the present invention.

FIG. 3 best illustrates the dovetail connection members interengaged to connect a suture storage box 12 to a suture display box 10. Bottom wall 18 of suture display box 10 is provided with a dovetail connection member 24 which cooperates with dovetail connection member 38 of top wall 26 of suture storage box 12. Dovetail connection member 38 is slid into dovetail connection member 24 to secure suture storage box 12 to suture display box 10 as shown. Bottom wall 28 of suture storage box 12 is provided with dovetail connection member 38 as shown, and side walls 20 and 22 of suture display box 10 are provided with dovetail connection members 24 as illustrated.

Figure 4:
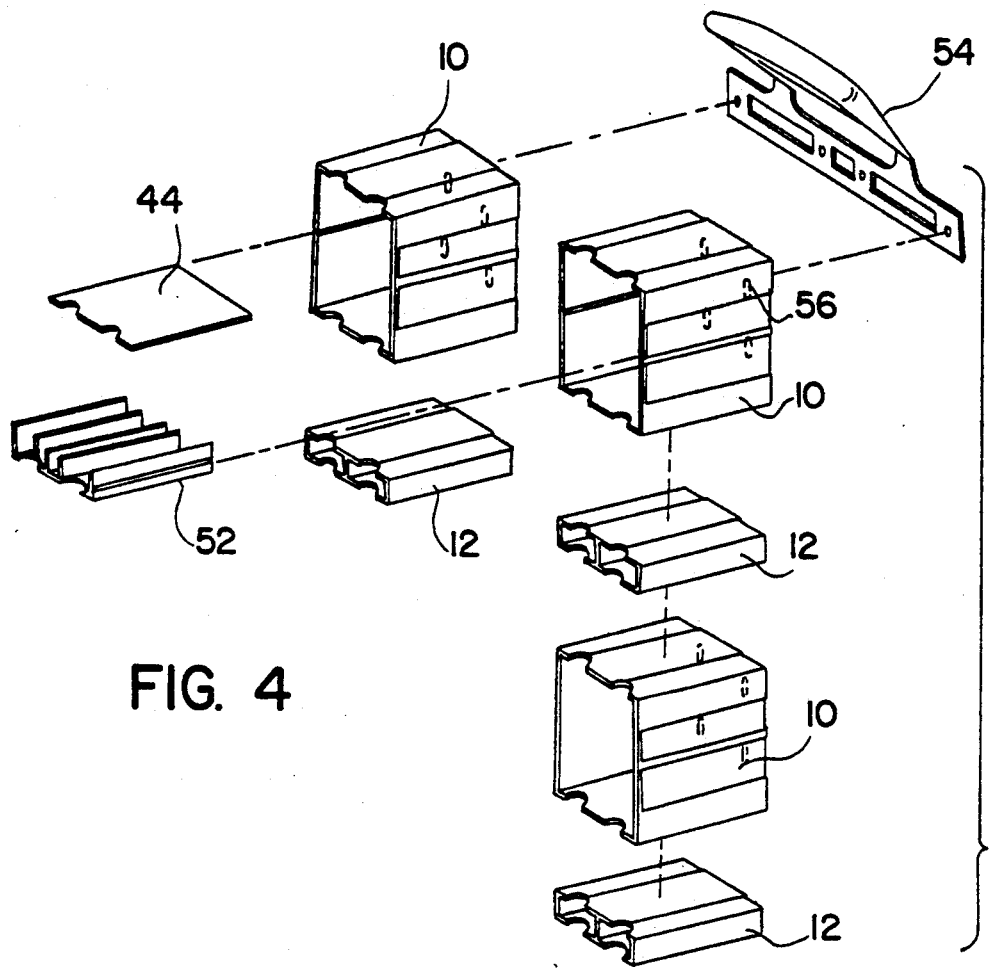
FIG. 4 illustrates an exploded perspective view of an alternate embodiment of the suture display cabinet of the present invention.

FIG. 4 illustrates a first alternate embodiment of the suture display cabinet of the present invention. The suture display cabinet 60, shown in FIG. 5, comprises a plurality of suture display boxes 10 and suture storage boxes 12 interconnected by means of the dovetail connection members to form an array of boxes which comprise the suture display cabinet. Preferably, from the embodiment shown in FIG. 4 and 5, two rows of three suture display boxes 10, having suture storage boxes 12 attached to the bottom wall thereof, are provided. Suture display boxes 10 may include shelves 44, or alternately shelves 52 which are provided with a plurality of upstanding vertically disposed partitions as shown in FIG. 4. A handle member 54 is provided to facilitate transporting the suture display cabinet 60 from place to place, preferably within an operating room. Handle 54 is secured preferably to the back wall 16 of suture display boxes 10 as shown. One preferred method of securing handle 54 to suture display boxes 10 is through pins or hook members which are secured within key hole slots 56 positioned on back wall 16 of each of the suture display boxes 10. Key hole slots 56 also provide a means for mounting suture display cabinet 60 on a wall if so desired.

Figure 5:
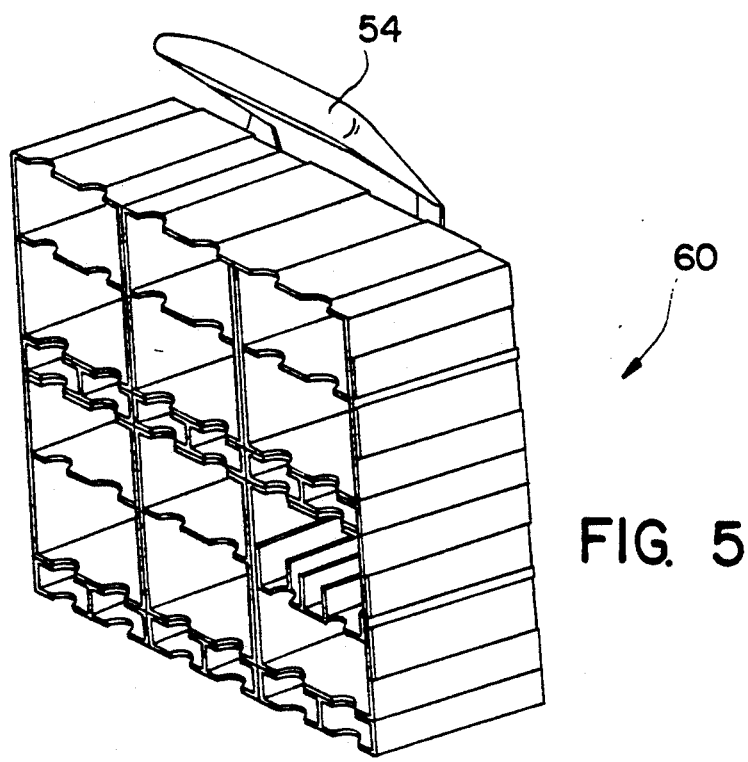
FIG. 5 illustrates a perspective view of the assembled suture display cabinet of FIG. 4.
Figure 6:
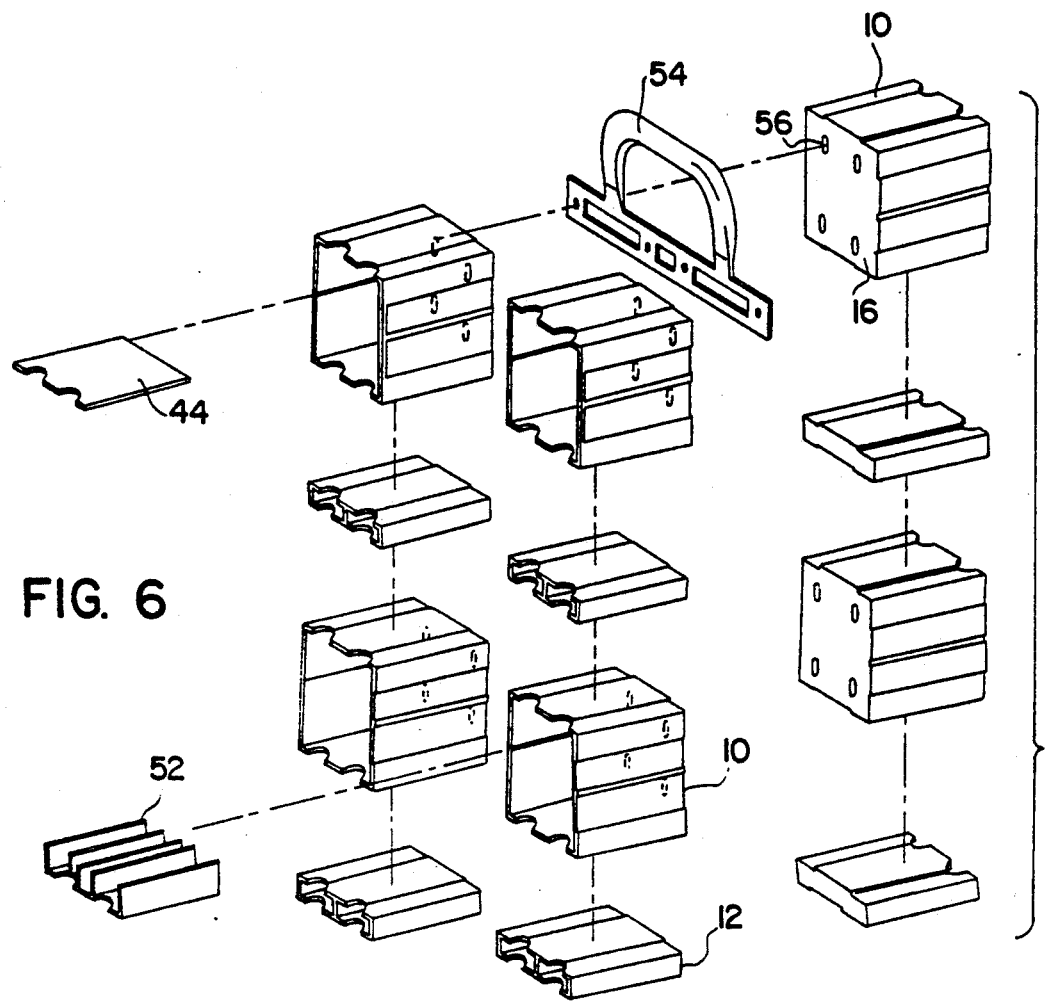
FIG. 6 illustrates an exploded perspective view of a second alternate embodiment of the suture display cabinet of the present invention.
Figure 7:
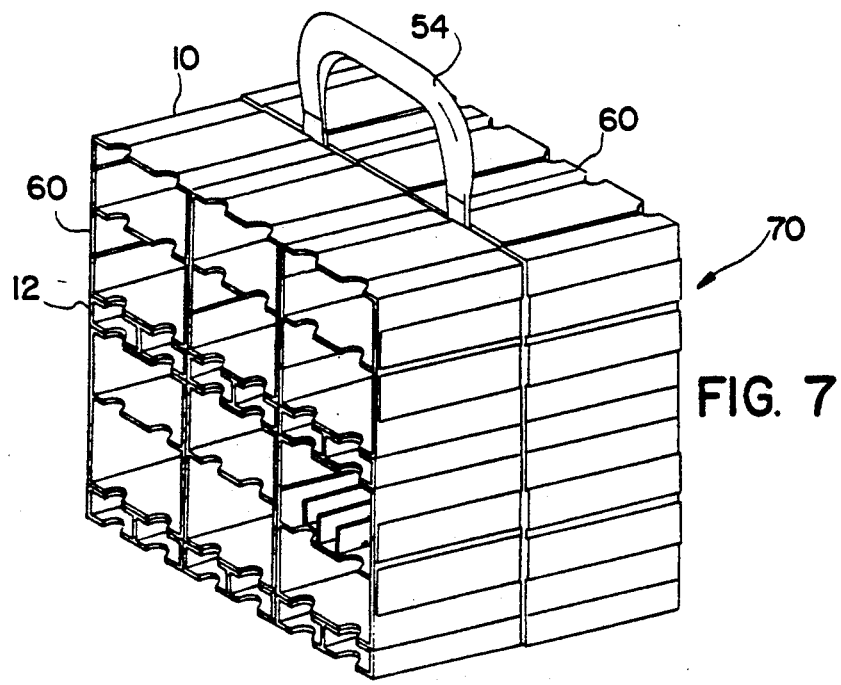
FIG. 7 illustrates an assembled perspective view of the suture display cabinet of FIG. 7.

FIGS. 6 and 7 illustrate a second alternate embodiment of the suture display cabinet of the present invention. Suture display cabinet 70 essentially comprises two suture display cabinets 60 as shown in FIG. 5 positioned back to back with handle 54 secured therebetween. As shown, two rows of three suture display boxes 10 and their associated suture storage boxes 12 are positioned back to back to form suture display cabinet 70. Handle 54 is secured to the back walls 16 of the uppermost suture display boxes 10 utilizing key hole slots 56 to secure the handle therebetween. Of course, any means may be used to secure handle member 54 to cabinet 70, such as adhesives, heat staking or the like.

Figure 8:
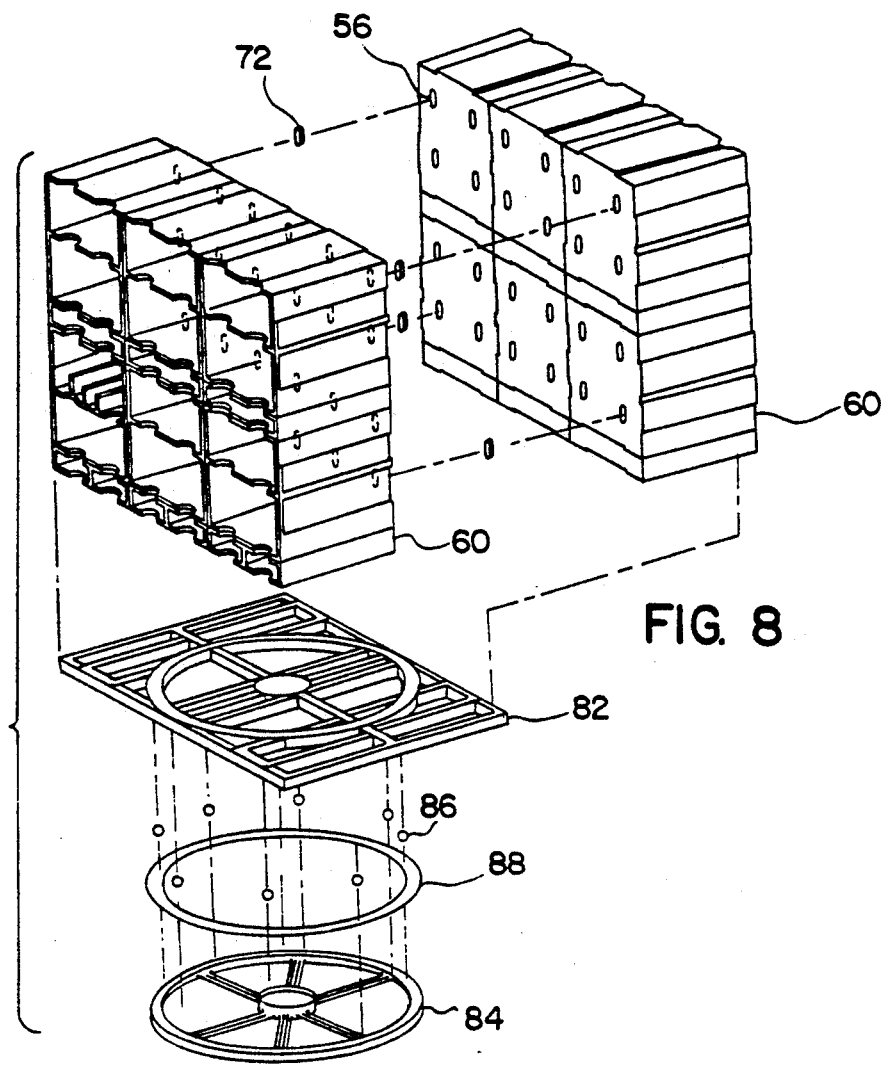
FIG. 8 illustrates an exploded perspective view of a third alternate embodiment of the suture display cabinet of the present invention.
Figure 9:
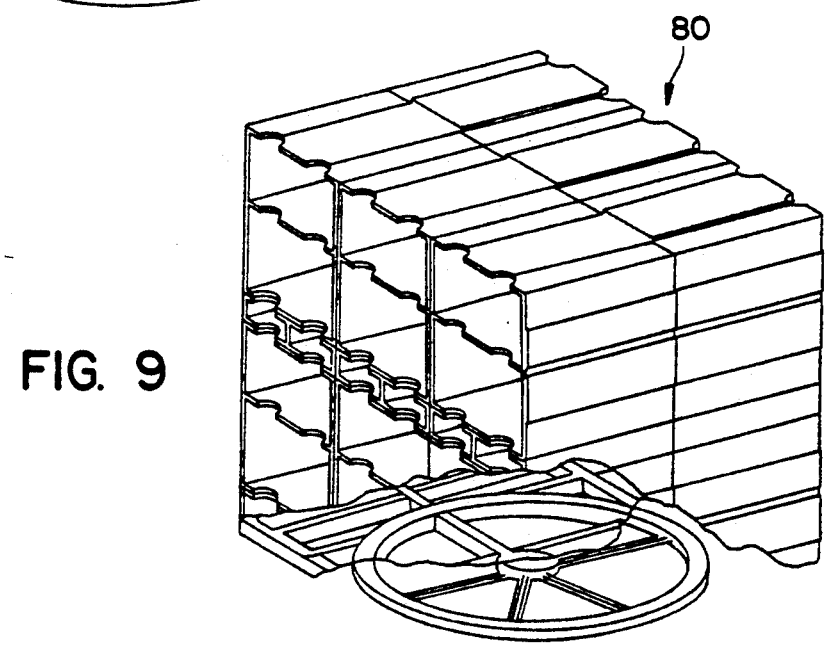
FIG. 9 illustrates an assembled perspective view, in partial cut-away, of the suture display cabinet of FIG. 8.

FIGS. 8 and 9 illustrate a third alternate embodiment of the suture display cabinet of the present invention. The suture display cabinet 80 is similar to suture display cabinet 70 in that two rows of suture display boxes 10 and suture storage boxes 12 forming cabinet 60 are positioned one on top another and then joined through the provision of pins 72 to a second cabinet 60 forming a set of two rows as shown. Pins 72 preferably join the back to back boxes through key hole slots 56. Suture display cabinet 80 is then positioned on a tray member 82 which includes a base 84 having ball bearings 86 secured in a ring member 88. Tray 82 revolves about base 84 over ball bearings 86, which creates a lazy-susan type arrangement which allows suture display cabinet 80 to revolve around base 84. This provides 360° access to sutures stored in the cabinet 80 for surgical personnel during use.

Figure 10:
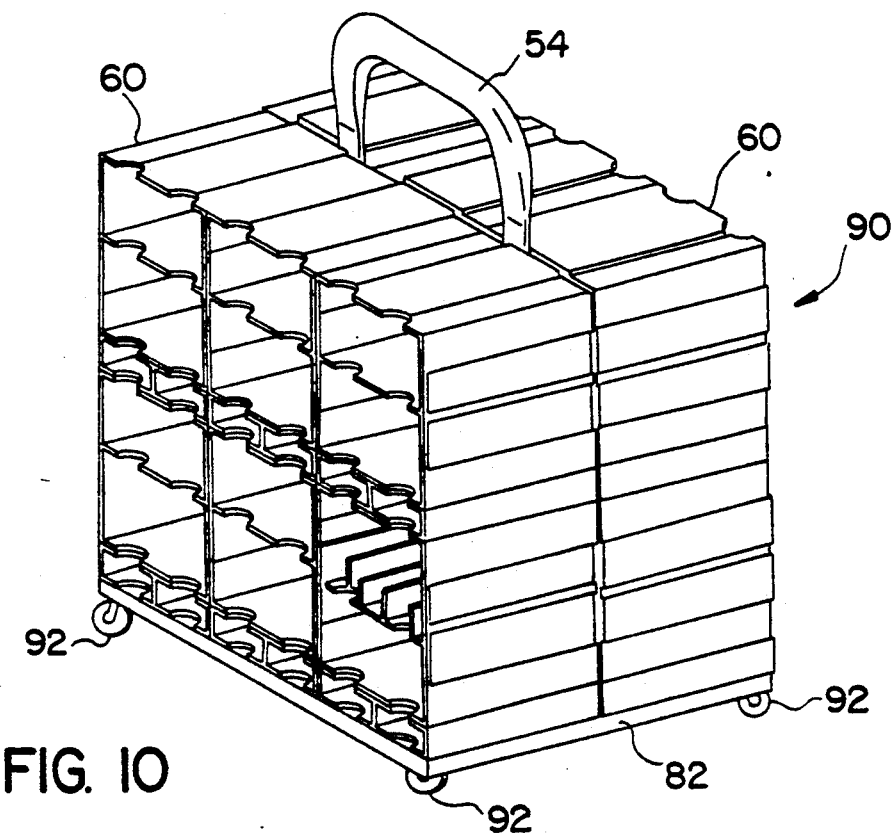
FIG. 10 illustrates a fourth alternate embodiment of the suture display cabinet of the present invention.

FIG. 10 illustrates a fourth alternate embodiment of the suture display cabinet of the present invention. Cabinet 90 is similar to cabinet 70 in that two back to back display cabinets 60 are provided with a handle member 54 to facilitate moving suture display cabinet 90 from place to place. To this end, a tray 82 is provided having casters or wheels 92 positioned thereon to allow cabinet 90 to be rolled from place to place for use at various locations.

Figure 11:
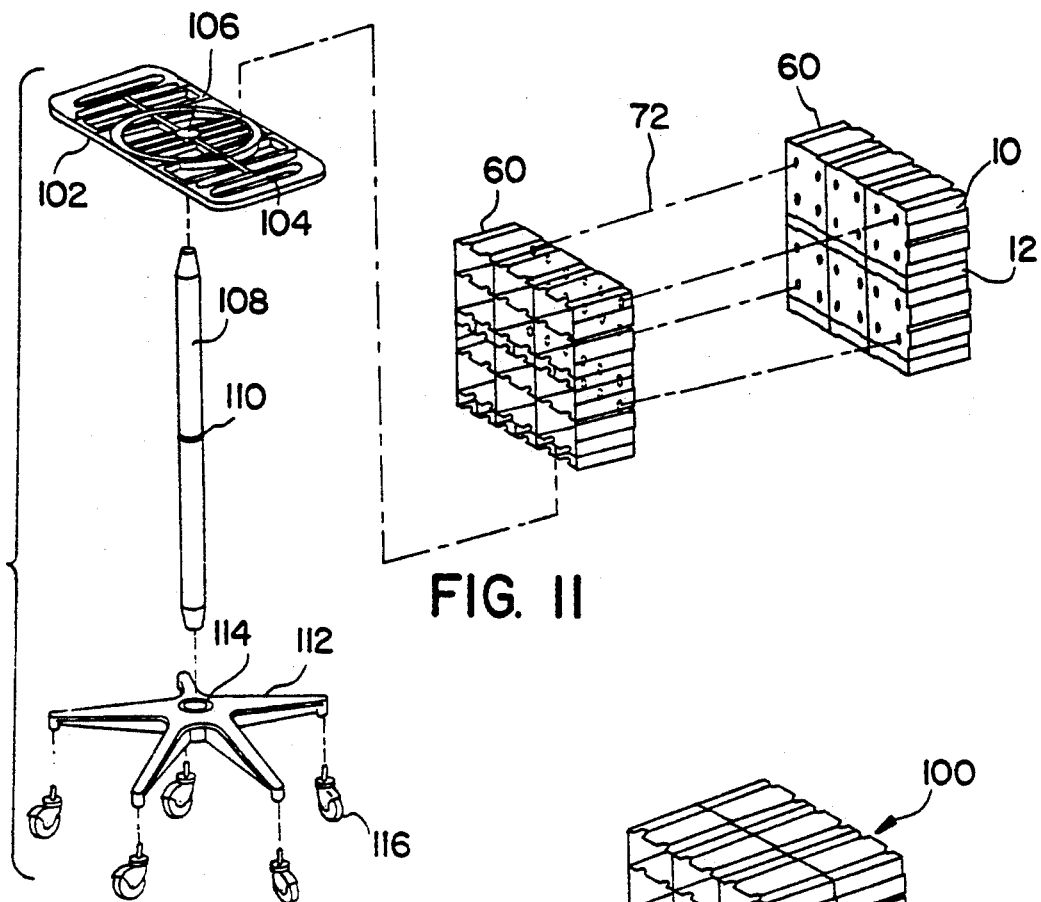
FIG. 11 illustrates an exploded perspective view of a fifth alternate embodiment of the suture display cabinet of the present invention.
Figure 12:
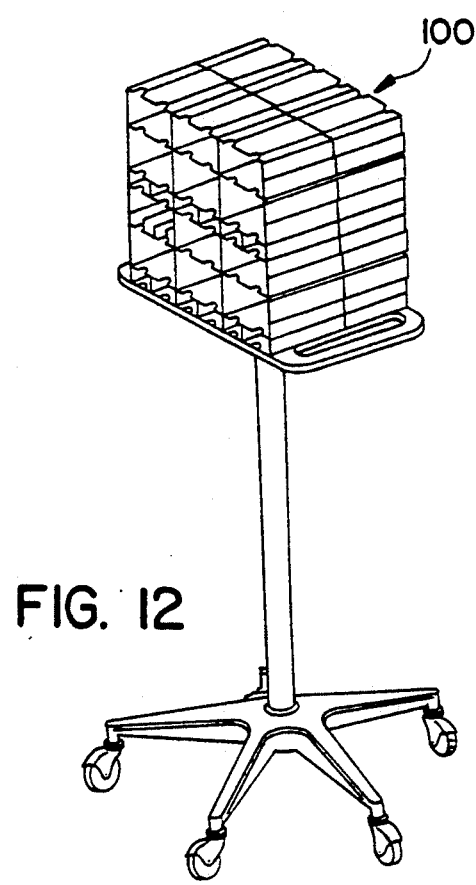
FIG. 12 illustrates an assembled perspective view of the suture display cabinet of FIG. 11.

FIGS. 11 and 12 illustrate a fifth alternate embodiment of the suture display cabinet of the present invention. Suture display cabinet 100 utilizes the back to back construction of cabinets 60 shown in FIG. 7, in which a suture display cabinet similar to suture display cabinet 70 is positioned on a tray member 102. The back to back construction of the suture display boxes 10 and suture storage boxes 12 are secured through the provision of pins 72 as described above. Suture display cabinet 100 is positioned on tray 102 which is then secured to a pole 108 at pole mount 106. Pole 108 is further secured to a pedestal base 112 at pole mount 114. Pedestal base 112 is provided with wheels or casters 116 to facilitate rolling suture display cabinet 100 from place to place. Tray 102 is provided with handle members 104 to provide a means for controlling cabinet 100 while it is being moved. Pole 108 is provided with a break or partition line 112, which allows pole 108 to be shortened or raised to vary the height at which suture display cabinet 100 is maintained. Preferably, pole 108 is telescopic in that it can be height adjustable to suit the particular needs of the personnel in the operating environment.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered in the scope of the invention.

What is claimed is:

1. A suture display cabinet comprising;
   a plurality of suture display boxes, each box being dimensioned for displaying at least one vertically disposed column of individual suture packages stacked one on top another, each box having a back wall, two side walls, a top and a bottom wall, said side walls, top wall and bottom wall of each box having an externally positioned dovetail connection member, ad said back wall of each box having at least one key hole slot therein for connecting said boxes to a support structure;
   a plurality of single suture storage boxes, said storage boxes each having a back wall, two side walls, a top and bottom wall, said top and bottom walls corresponding in size to said top and bottom walls of said suture display boxes, said top and bottom walls each having an externally positioned dovetail connection member,
   wherein said top wall of said suture storage boxes are modularly connected to said bottom wall of said suture display boxes, and said suture display boxes are modularly connected to adjacent side walls of said suture display boxes to form individual rows of interconnected boxes, and wherein said bottom wall of each said suture storage boxes of said individual rows of interconnected boxes are modularly connected to corresponding walls of said suture display boxes of said individual rows of interconnected boxes to form said suture display cabinet; and
   means secured to said suture display cabinet for enhancing portability of said suture display cabinet.

2. A suture display cabinet comprising
   a first row of suture display boxes;
   a second row of suture display boxes;
   each suture display box including a back wall, two side walls, a top wall and a bottom wall, said top, bottom and side walls each including a dovetail connection member for joining said boxes to each other to form each of said rows;

wherein said first row and said second row are arranged back-to-back along said back walls to form said display cabinet; and a tray member upon which said first and second rows are mounted, said tray member having handle members secured thereto to facilitate lifting and carrying said display cabinet.

3. A suture display cabinet according to claim 2, said cabinet further comprising a row of suture storage boxes positioned beneath each row of suture display boxes, said suture storage boxes having a back wall, two side walls, a top wall and a bottom wall, said top and bottom walls each having a dovetail connection member for joining said suture storage boxes to said suture display boxes.

4. A suture display cabinet according to claim 3, wherein said suture display boxes are dimensioned to accommodate at least one column of suture packages stacked one on top another, and further wherein said suture storage boxes are dimensioned to be of the same width and depth as said suture display boxes for storing individual ones of said suture packages.

5. A suture display cabinet according to claim 3, said cabinet further comprising a plurality of rows stacked in back-to-back relation on top of said first and second rows, said plurality of rows joined to said first and second rows and each other by dovetail connection members on said top and bottom walls of said suture display boxes and said suture storage boxes.

6. A suture display cabinet comprising:
a first row of suture display boxes;
a second row of suture display boxes;
each suture display box including a back wall, two side walls, a top wall and a bottom wall, said top, bottom and side walls each including a dovetail connection member for joining said boxes to each other to form each of said rows;
wherein said first row and said second row are arranged back-to-back along said back walls to form said display cabinet and
a tray member upon which said first and second rows are mounted, said tray member having a plurality of casters secured thereto to facilitate transport of said display cabinet.

7. A suture display cabinet according to claim 6, wherein said revolving pedestal comprises a turntable arrangement, said turntable including a base member having a plurality of ball bearings to facilitate rotation.

8. A suture display cabinet according to claim 7, said cabinet further comprising a base having casters and an extended pole member, said tray member and revolving pedestal being mounted on said pole member, and said pole member being attached to said base, wherein said tray member and revolving pedestal are detachably mounted to said pole member.

9. A suture display cabinet comprising:
a plurality of suture display boxes, each box being dimensioned for displaying at least one vertically disposed column of individual suture packages stacked one on top another, each box having a back wall, two side walls, a top and a bottom wall, said side walls, top wall and bottom wall of each box having an externally positioned dovetail connection member, and said back wall of each box having at least one key hole slot therein;
a plurality of single suture storage boxes, said storage boxes each having a back wall, two side walls, a top and bottom wall, said top and bottom walls corresponding in size to said top and bottom walls of said suture display boxes, said top and bottom walls each having an externally positioned dovetail connection member,
wherein said top and bottom walls of said suture storage boxes are modularly connected to said top and bottom walls of said suture display boxes, and said suture display boxes are modularly connected to adjacent side walls of said suture display boxes to form at least first and second rows of interconnected boxes, said second row being positioned adjacent said first row such that said back wall of each of said boxes of said second row abuts said back wall of each said boxes of said first row, said first row and said second row being connected by a plurality of pins fixedly secured in said key hole slots in said back walls to form said suture display cabinet.

10. A suture display cabinet according to claim 9, wherein said pole member is telescopically extendable to raise and lower the height of said display cabinet.

11. A suture display cabinet according to claim 9, wherein said tray is detachably mounted to said pole member for removing said cabinet from said pole member and base.

12. A suture display cabinet comprising
a first row of suture display boxes;
a second row of suture display boxes;
each suture display box including a back wall, two side walls, a top wall and a bottom wall, said top, bottom and side walls each including a dovetail connection member for joining said boxes to each other to form each of said rows;
wherein said first row and said second row are arranged back-to-back along said back walls to form said display cabinet;
a handle member secured to and positioned between said back walls of said first and second rows of suture display boxes; and
a tray member upon which said first and second rows are mounted, said tray member having means for enhancing portability secured thereto.

13. A suture display cabinet comprising:
a first row of suture display boxes;
a second row of suture display boxes;
each suture display box including a back wall, two side walls, a to wall and a bottom wall, said top, bottom and side walls each including a dovetail connection member for joining said boxes to each other to form each of said rows;
wherein said first row and said second row are arranged back-to-back along said back walls to form said display cabinet; and
a tray member upon which said first and second rows are mounted, said tray member having a revolving pedestal for rotating said display cabinet and said tray member.

14. A suture display cabinet comprising;
a first row of suture display boxes;
a second row of suture display boxes;
each suture display box including a back wall, two side walls, a top wall and a bottom wall, said top, bottom and side walls each including a dovetail connection member for joining said boxes to each other to form each of said rows
wherein said first row and said second row are arranged back-to-back along said back walls to form said display cabinet;

a tray member upon which said first and second rows are mounted;

a base having a plurality of casters; and an extended pole member positioned between said tray member and said base to facilitate transport of said display cabinet.

15. A suture display cabinet comprising;

a plurality of suture display boxes, each box being dimensioned for displaying at least one vertically disposed column of individual suture packages stacked one on top another, each box having a back wall, two side walls, a top and a bottom wall, said side walls, top wall and bottom wall of each box having an externally positioned dovetail connection member;

a plurality of single suture storage boxes, said storage boxes each having a back wall, two side walls, a top ad bottom wall, said top and bottom walls corresponding in size to said top and bottom walls of said suture display boxes, said top and bottom walls each having an externally positioned dovetail connection member, wherein said top wall of said suture storage boxes are modularly connected to said bottom wall of said suture display boxes, and said suture display boxes are modularly connected to adjacent side walls of said suture display boxes to form individual rows of interconnected boxes, and wherein said bottom wall of each said suture storage boxes of said individual rows of interconnected boxes are modularly connected to corresponding walls of said suture display boxes of said individual rows of interconnected boxes to form said suture display cabinet;

a tray member upon which said suture display cabinet is mounted; and a base having a plurality of wheels and secured to said tray member.

16. A suture display cabinet comprising a plurality of suture display boxes, each box being dimensioned for displaying at least one vertically disposed column of individual suture packages stacked one on top another, each box having a back wall, two side walls, a top and a bottom wall, said side walls, top wall and bottom wall of each box having an externally positioned dovetail connection member;

a plurality of single suture storage boxes, said storage boxes each having a back wall, two side walls, a top and bottom wall, said top and bottom walls corresponding in size to said top and bottom walls of said suture display boxes, said top and bottom walls each having an externally positioned dovetail connection member, wherein said top and bottom walls of said suture storage boxes are modularly connected to said top and bottom walls of said suture display boxes, and said suture display boxes are modularly connected to adjacent side walls of said suture display boxes to form at least one row of interconnected boxes to form said suture display cabinet; and rotating means secured to said suture display cabinet for rotating said suture display cabinet, said rotating means including a turntable arrangement having a base member rotatably mounted to a support member with friction reducing means disposed therebetween to facilitate rotation.

* * * * *